United States Patent
Kuusela et al.

(10) Patent No.: US 11,158,408 B2
(45) Date of Patent: *Oct. 26, 2021

(54) CLINICAL GOAL TREATMENT PLANNING AND OPTIMIZATION

(71) Applicant: Varian Medical Systems International AG, Cham (CH)

(72) Inventors: Esa Kuusela, Espoo (FI); Lauri Halko, Helsinki (FI)

(73) Assignee: Varian Medical Systems International AG, Cham (CH)

(*) Notice: Subject to any disclaimer, the term of this patent is extended or adjusted under 35 U.S.C. 154(b) by 114 days.

This patent is subject to a terminal disclaimer.

(21) Appl. No.: 16/580,488

(22) Filed: Sep. 24, 2019

(65) Prior Publication Data
US 2020/0043580 A1 Feb. 6, 2020

Related U.S. Application Data

(63) Continuation of application No. 14/866,587, filed on Sep. 25, 2015, now Pat. No. 10,446,265.

(51) Int. Cl.
*G16H 10/60* (2018.01)
*G16H 50/30* (2018.01)
(Continued)

(52) U.S. Cl.
CPC ........... *G16H 10/60* (2018.01); *A61N 5/1031* (2013.01); *A61N 5/1045* (2013.01); *G06F 19/00* (2013.01);
(Continued)

(58) Field of Classification Search
CPC .... A61N 5/1031; A61N 5/1045; G16H 10/60; G16H 20/40; G16H 20/10; G16H 50/30; G06F 19/3456; G06F 19/00
(Continued)

(56) References Cited

U.S. PATENT DOCUMENTS

2005/0111621 A1* 5/2005 Riker .................... G16H 70/20
378/65
2006/0256915 A1 11/2006 Otto et al.
(Continued)

OTHER PUBLICATIONS

Holdsworth et al., A Hierarchical Evolutionary Algorithm For Multiobjective Optimization In IMRT, Aug. 27, 2010, Medical Physics, 37: 4986-4997 (Year: 2010).*
(Continued)

*Primary Examiner* — Joy Chng

(57) ABSTRACT

An apparatus for developing an intensity-modulated radiation therapy treatment plan includes a memory that stores machine instructions and a processor that executes the machine instructions to receive a clinical goal associated with the treatment plan as a user input. The processor further executes the machine instructions to determine a plan objective based on the clinical goal, generate a cost function comprising a term based on the plan objective, and assign an initial value to a parameter associated with the term. The processor also executes the machine instructions to identify a microstate that results in a reduced value associated with the cost function, evaluate a fulfillment level associated with the clinical goal, and adjust the value of the parameter to improve the fulfillment level.

20 Claims, 3 Drawing Sheets

(51) Int. Cl.
*A61N 5/10* (2006.01)
*G16H 20/10* (2018.01)
*G16H 20/40* (2018.01)
*G06F 19/00* (2018.01)

(52) U.S. Cl.
CPC ............. *G16H 20/10* (2018.01); *G16H 20/40* (2018.01); *G16H 50/30* (2018.01)

(58) Field of Classification Search
USPC ........................................................ 705/2–3
See application file for complete search history.

(56) References Cited

U.S. PATENT DOCUMENTS

| | | |
|---|---|---|
| 2007/0003011 A1 | 1/2007 | Lane |
| 2012/0203053 A1 | 8/2012 | Kilby et al. |
| 2015/0087879 A1* | 3/2015 | Nelms .................. A61B 6/5294 600/1 |

OTHER PUBLICATIONS

Verhey et al., Issues in optimization for planning of intensity-modulated radiation therapy, Seminars in Radiation Oncology, vol. 12, Issue 3, Jul. 2002, pp. 210-218, ISSN 1053-4296, https://doi.org/10.1053/srao.2002.32434. (Year: 2002).*

* cited by examiner

CLINICAL GOAL TREATMENT PLANNING AND OPTIMIZATION

CROSS-REFERENCE TO RELATED APPLICATIONS

This application claims the benefit of and priority to patent application Ser. No. 14/866,587, with a filing date of Sep. 25, 2015, now U.S. Pat. No. 10,446,265, which is hereby incorporated by reference in its entirety.

TECHNICAL FIELD

This description relates generally to radiation therapy planning, and more particularly to developing a radiation therapy plan based on clinical goals.

BACKGROUND

Intensity-modulated radiation therapy (IMRT) is an advanced type of high-precision radiotherapy used to deliver precise radiation doses in medical procedures. IMRT modulates the intensity of multiple radiation fields originating from different directions to primarily focus on a region of the patient's body that generally conforms to the shape of a target volume, such as a malignant tumor, while exposing surrounding normal tissue to reduced levels of radiation. Typically, a detailed treatment plan is developed using computed tomography (CT) or magnetic resonance imaging (MM) of the patient, along with computerized dose calculations to determine the dose intensity pattern.

In general, IMRT treatment plan optimization processes have been based on a cost function, which scores the achieved dose distribution. The cost function generally is defined such that more desirable treatment plans are associated with a microstate that results in relatively reduced cost function values. The microstate generally includes parameters needed to deliver the dose to the patient. The cost function typically is interactively defined, or specified, by a user, such as a medical technician or a physician, to develop the treatment plan with respect to certain machine parameters, optimal fluence, or the like.

In a typical optimization process, the user employs a set of treatment planning tools to specify the cost function contribution from various factors, such as requested target distributions, the dose level of organs-at-risk (OAR), dose distribution in normal tissue, or the like. In practice, the user generally specifies a set of optimization objectives, each of which is correlated with a term of the total cost function. Optimization objectives include, for example, dose-volume-histogram (DVH) objectives, normal tissue objectives (NTO), and so forth.

Existing treatment plan optimization methodologies can have drawbacks when used to develop radiation therapy plans. Defining the cost function to take into account clinical goals can involve a complex, often iterative, process requiring significant clinical experience. In general, the user has limited options with regard to plan improvement. Some plan details, for example, attaining a desired level of normalization, can be relatively difficult to control.

In other cases, the clinical goal definitions allow for multiple treatment plans, but it can be difficult to determine which of the plans is dosimetrically superior. In such cases, additional optional goals have been applied to the plan.

In addition, the dose distribution for multiple regions of normal tissue is controlled by a single NTO, which cannot guarantee achievement of clinical goals, and related parameters must be manually set by the user to comply with intended clinical goals. As a result, it often can be necessary to define virtual structures, that is, specified spatial regions having no direct anatomical function, in an attempt to control normal tissue exposures, for example, in the vicinity of target volumes or near the skin.

SUMMARY

According to one embodiment of the present invention, an apparatus for developing an intensity-modulated radiation therapy treatment plan includes a memory that stores machine instructions and a processor that executes the machine instructions to receive a clinical goal associated with the treatment plan as a user input. The processor further executes the machine instructions to determine a plan objective based on the clinical goal, generate a cost function comprising a term based on the plan objective, and assign an initial estimate of a value of a parameter associated with the term. The processor also executes the machine instructions to identify a microstate that results in a reduced value associated with the cost function, evaluate a fulfillment level associated with the clinical goal, and adjust the value of the parameter to improve the fulfillment level.

According to another embodiment of the present invention, a computer-implemented method for developing an intensity-modulated radiation therapy treatment plan includes determining a plan objective based on a clinical goal associated with the treatment plan, and generating a cost function comprising a term based on the plan objective. The term includes a parameter. The method further includes identifying a microstate that results in a reduced value associated with the cost function, evaluating a fulfillment level associated with the clinical goal, and adjusting a value associated with the parameter to improve the fulfillment level.

According to yet another embodiment of the present invention, a computer program product includes a non-transitory, computer-readable storage medium encoded with instructions adapted to be executed by a processor to implement determining a plan objective based on a clinical goal associated with the treatment plan, and generating a cost function comprising a term based on the plan objective. The term includes a parameter. The instructions are further adapted to implement identifying a microstate that results in a reduced value associated with the cost function, evaluating a fulfillment level associated with the clinical goal, and adjusting a value associated with the parameter to improve the fulfillment level.

The details of one or more embodiments of the invention are set forth in the accompanying drawings and the description below. Other features, objects, and advantages of the invention will be apparent from the description and drawings, and from the claims.

DETAILED DESCRIPTION

An embodiment of the present invention provides an intensity-modulated radiation therapy (IMRT) treatment planning device that can be employed by a user, such as a medical technician or a physician, to aid the development of a therapeutic medical treatment plan, for example, to treat a malignant tumor in a cancer patient. In various embodiments, the IMRT treatment planning device generates a treatment plan solution that fulfills all of the corresponding clinical goals specified by the user, as many of the user-specified clinical goals as possible, or a subset of the user-specified goals in accordance with user-specified priorities.

An embodiment of the IMRT treatment planning device converts clinical goals input by the user into plan objectives and creates a cost function based on parameters corresponding to the objectives. The IMRT treatment planning device iteratively determines an appropriate microstate, or microscopic state, that results in a relatively low cost function value and determines a corresponding treatment plan solution. The treatment plan solution is generated based on a selected set of machine parameters, such as a selected field geometry, a selected monitor unit (MU) limit, or the like.

In various embodiments, the IMRT treatment planning device receives clinical goals, for example, regarding the dose distributions with respect to a target volume, an organ-at-risk (OAR) in the vicinity of the target volume, or other specified or unspecified normal tissue, and develops a corresponding treatment plan solution. In some embodiments, the IMRT treatment planning device receives residual goals, that is, additional clinical goals that generally may not be fully achieved, but can be at least partially achieved by the treatment plan solution.

As used in this disclosure, the terms "optimize," "optimal," "optimization," and related terms are used not in a strict sense to indicate an absolute condition, as in the best possible solution, but rather, to imply a relative improvement, a relatively favorable condition, or a relatively preferable solution. The explicit or implicit meaning attributed to these terms in any other context should not determine the intended meaning or usage herein.

Figure 1:
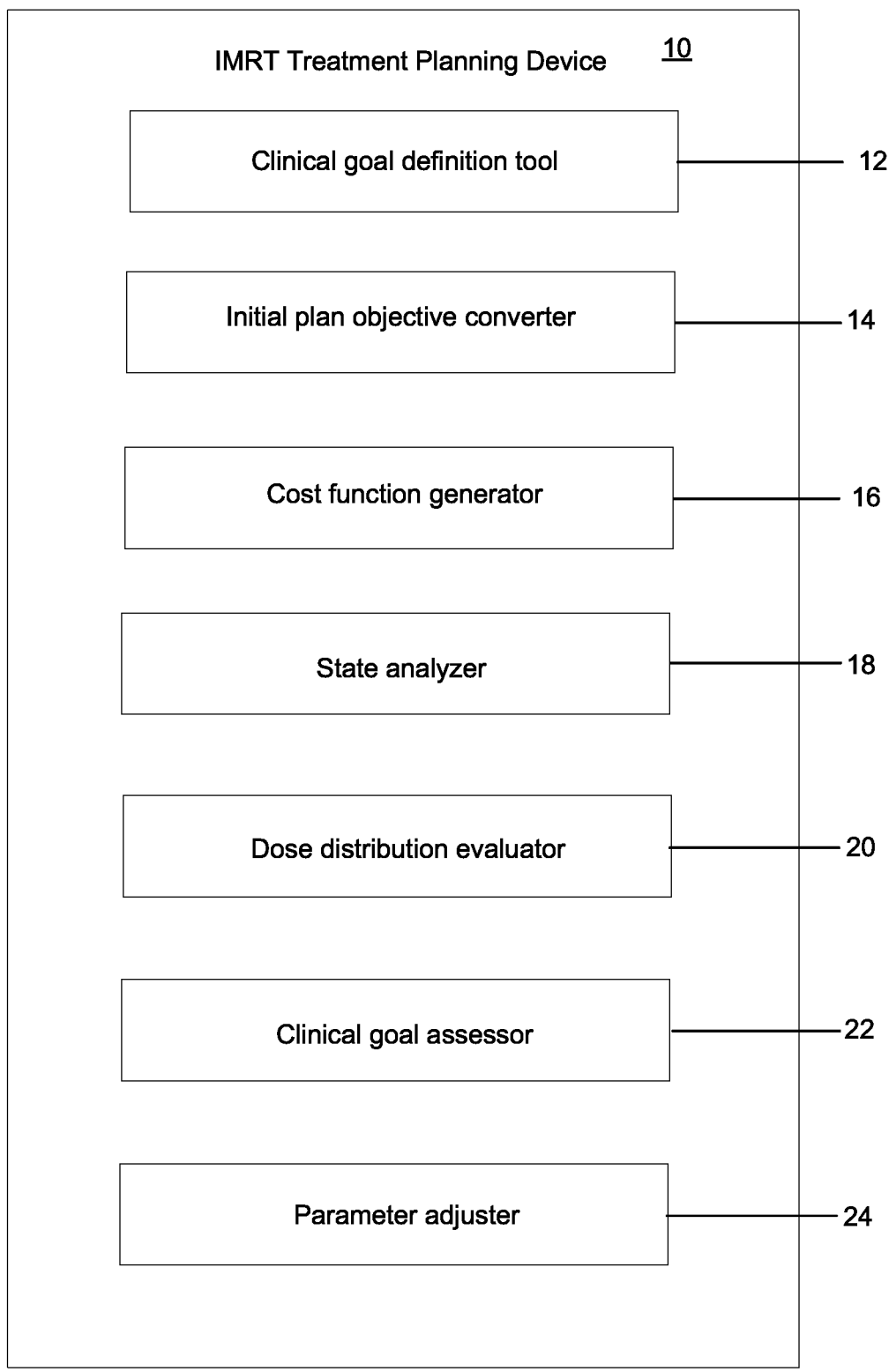
FIG. 1 is a block diagram illustrating an exemplary intensity-modulated radiation therapy (IMRT) treatment planning device in accordance with an embodiment of the present invention.

An embodiment of the present invention is shown in FIG. 1, which illustrates an exemplary intensity-modulated radiation therapy (IMRT) treatment planning device 10 that employs a treatment plan metaoptimization scheme to develop an appropriate IMRT treatment plan solution for a patient. The IMRT treatment planning device 10 includes a clinical goal definition tool 12, an initial plan objective converter 14, a cost function generator 16, a state analyzer 18, a dose distribution evaluator 20, a clinical goal assessor 22, and a parameter adjuster 24.

The clinical goal definition tool 12 receives clinical goal input from an IMRT treatment planning device user, such as a medical technician or a physician. The input clinical goals can include any number of desired factors related to treatment outcome, for example, target volume dose distribution, organ-at-risk dose distributions, other normal tissue dose distributions, other spatial dose distributions, maximum dose, mean dose, minimum dose, or the like. In some embodiments, the input clinical goals also include one or more residual goals to be at least partially fulfilled, if possible, in addition to attainment of primary clinical goals.

In addition, in an embodiment, the clinical goal definition tool 12 receives priority input from the IMRT treatment planning device user. For example, the clinical goal definition tool 12 receives a numeric rank regarding one or more of the input clinical goals indicating the relative priority of the goals with respect to one another. The priorities may indicate, for example, that a particular clinical goal is to be fulfilled, if possible, at the expense of fulfillment of lower priority goals. Thus, the input priorities may be used to guide the attempted optimization of the treatment plan.

The initial plan objective converter 14 creates a set of plan objectives based on the received clinical goals. In an embodiment, the initial plan objective converter 14 creates a single plan objective corresponding to each clinical goal. In other embodiments, the initial plan objective converter 14 creates multiple objectives corresponding to one or more of the clinical goals. An example plan objective may seek to control a dose differential based on a prescription dose and a predicted actual dose at a particular point in a patient volume.

The cost function generator 16 generates a cost function that incorporates the plan objectives. For example, the cost function generator 16 may design individual cost terms corresponding to the plan objectives, and the value of the cost function may equal the sum of all the cost terms. Conventionally, the cost function generator 16 designs each of the cost function terms to minimize the value of the cost function when the corresponding plan objectives, and thus, the associated clinical goals, are attained.

An example cost term may include a summation or integral of dose differentials at multiple points throughout a particular volume along with a weighting factor. In various examples, the weighting factor may reflect, for example, the relative importance, or criticality, of meeting or not exceeding the prescription dose at all points in the volume.

In addition, one or more of the cost terms may include objective parameters that determine, at least in part, the value of the cost terms, or plan objectives. Free objective parameter values are determined during a treatment plan metaoptimization process. In an embodiment, each plan objective is defined as a function of a single free parameter. In another embodiment, each plan objective includes as few free parameters as practicable. Thus, the specific cost function becomes a function of the objective parameters.

Before the metaoptimization process is performed, the cost function generator 16 determines an initial value for each of the objective parameters. In various embodiments, initial objective parameter value determination is aided by a dose-volume histogram (DVH) estimation model or another knowledge-based approach.

In an embodiment, at least some of the objective parameters correspond to one or more underlying factors related to the microstate. The microstate generally includes all parameters needed to deliver the dose to the patient. The cost function is used to attain a near-optimal microstate based on the clinical goals. In general, the metaoptimization process attempts to optimize the free objective parameters such that all of the clinical goals are fulfilled, or such that as many clinical goals as possible, in order of priority, are fulfilled. As a result, the dose distribution related to the microstate that minimizes the cost function becomes a function of the objective parameters.

The state analyzer 18 determines the microstate that minimizes the value of the current cost function. In some embodiments, for example, in order to improve system performance, the selected microstate represents a non-optimal solution for the current cost function. In this case, a solution may be selected based on convergence towards an optimal solution. For example, in an embodiment, a single iteration or relatively few iterations are performed using an iterative gradient flow method to search for the microscopic state before the objective parameters are adjusted.

The dose distribution evaluator 20 determines the dose distribution resulting from the current microstate. For example, the dose distribution evaluator 20 may create a dose-volume histogram (DVH). The dose distribution evaluator 20 may implement any dose distribution estimation algorithm known in the art.

The clinical goal assessor 22 evaluates achievement of the clinical goals based on the current microstate. For example, the clinical goal assessor 22 analyzes the dose distribution information generated by the dose distribution evaluator 20 to determine whether each of the clinical goals has been attained.

The parameter adjuster 24 alters the values of the objective parameters in order to seek a microstate that minimizes the value of the cost function while producing a near-optimal clinical solution. In an embodiment, the parameter adjuster 24 projects gradients of the cost terms corresponding to individual plan objectives to estimate appropriate adjustments to the parameter values in order to construct a cost function with a related microscopic state that results in a treatment plan that relatively closely matches the clinical goals. The gradients represent forces tending to drive the objectives, and thus, the cost function.

For example, the local gradient of a cost term with respect to an objective parameter may be projected to estimate the parameter value at which the associated clinical goal would be marginally achieved. The resulting parameter value represents an estimated bound regarding modification of the parameter. In this manner, estimated bounds may be determined with regard to various competing objectives.

In an alternative embodiment, the parameter adjuster 24 anticipates dose distribution reactions to guide the adjustment of the objective parameters in the metaoptimization process. In general, any change made to an objective parameter causes a resultant reaction in the dose distribution. The reaction response may be extrapolated based on a response assumption, for example, assuming a linear response. The extrapolated response may be used to estimate the required amount of adjustment to the parameter needed to attain a desired change in the dose distribution, and thus, to meet a specified clinical goal. In a similar manner, it is possible to estimate the maximum adjustment to the parameter that will not violate another clinical goal.

In the case that it is not possible to simultaneously attain all of the clinical goals, the parameter adjuster 24 takes the specified priorities into account in determining which of the clinical goals to prioritize. For example, the parameter adjuster 24 may require that all plan objectives related to higher-priority clinical goals be met before attempting to fulfill a plan objective related to a lower-priority clinical goal.

Other embodiments are within the scope of the following claims. For example, in another implementation, the IMRT treatment planning device permits the user to directly specify generalized clinical goals related to normal tissue objectives (NTO). Thus, the user may specify, for example, "no dose larger than accepted to target in the normal tissue," or "no dose higher than 60% of the target dose level anywhere more than 6 centimeters away from the target."

The specified clinical goals are automatically converted into suitable objectives controlling the dose distribution in the normal tissue. For example, the IMRT treatment planning device designs a spatial objective that affects a region wherein all points share a common feature, such as "distance to the closest target is within specified range," effectively defining a shell for the union of the target. Any dose in the region above a preset objective dose level, such as slightly below the prescription dose level, cause the corresponding cost term to contribute to the total cost function.

NTO terms also may include more complex metrics, such as those used in dose distribution estimation algorithms. During the metaoptimization process, the individual contributions of the NTO terms to the total cost function are adjusted in order to attain the desired clinical goals. For example, the example preset objective dose level and an associated objective weight are tuned such that the corresponding clinical goal is met.

In another implementation, the IMRT treatment planning device can receive a residual goal and convert it into a suitable plan objective. The residual goal may be only partially attained while aiding convergence of the metaoptimization process toward a single solution. An example residual goal would be to reduce the dose level in a particular set of critical organs. In this case, the residual clinical goal could be converted into an objective represented by a constant multiplied by the dose level.

Another example would be to leave increasing margin around each clinical goal, which could be beneficial in situations where the plan quality might be reduced in some later treatment planning step, such as when converting optimal fluence to leaf sequence or subsequently calculating the dose distribution with a more accurate dose calculation algorithm.

In general, a single residual objective is sufficient to aid convergence, and a clinical counterpart is not strictly required. In addition, so long as the desired effect can be directly represented by a cost term in the cost function, the residual goal need not be precisely defined.

The systems described herein can offer advantages such as automatic conversion of specified clinical goals into plan objectives that can be optimized to produce a near-optimal treatment plan. Embodiments can automatically create treatment plans that fulfill specified normalization criteria, or that do not exceed a specified maximum dose for a particular organ-at-risk (OAR).

Figure 2:
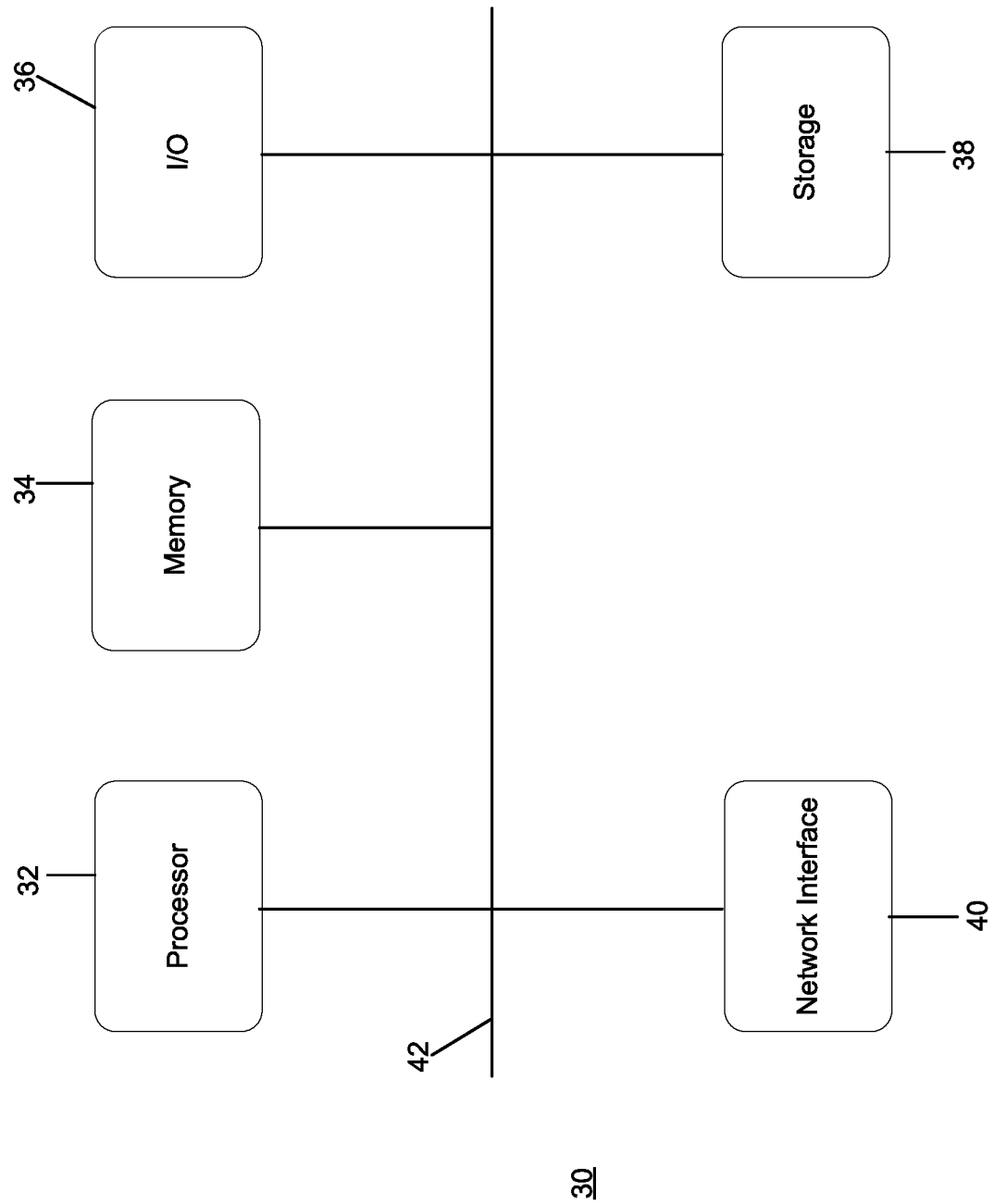
FIG. 2 is a schematic view depicting an exemplary general computing system that can implement the treatment planning device of FIG. 1.

As illustrated in FIG. 2, an exemplary general computing device 30 that can be employed in the intensity-modulated radiation therapy (IMRT) treatment planning device 10 of FIG. 1 includes a processor 32, a memory 34, an input/output device (I/O) 36 storage 38 and a network interface 40. The various components of the computing device 30 are coupled by a local data link 42, which in various embodiments incorporates, for example, an address bus, a data bus, a serial bus, a parallel bus, or any combination of these.

The computing device 30 communicates information to and requests input from the user or other devices by way of the I/O 36, which in various embodiments incorporates, for example, an interactive, menu-driven, visual display-based user interface, or graphical user interface (GUI). The computing device 30 may be coupled to a communication network by way of the network interface 40, which in various embodiments incorporates, for example, any combination of devices—as well as any associated software or firmware—configured to couple processor-based systems, including modems, access points, network interface cards, LAN or WAN interfaces, wireless or optical interfaces and the like, along with any associated transmission protocols, as may be desired or required by the design.

The computing device 30 can be used, for example, to implement the functions of the components of the IMRT treatment planning device 10 of FIG. 1. In various embodiments, the computing device 30 can include, for example, a server, a controller, a workstation, a mainframe computer, personal computer (PC), a note pad, a computing tablet, a personal digital assistant (PDA), a smart phone, a wearable device, or the like. Programming code, such as source code, object code or executable code, stored on a computer-readable medium, such as the storage 38 or a peripheral storage component coupled to the computing device 30, can be loaded into the memory 34 and executed by the processor 32 in order to perform the functions of the IMRT treatment planning device 10.

Figure 3:
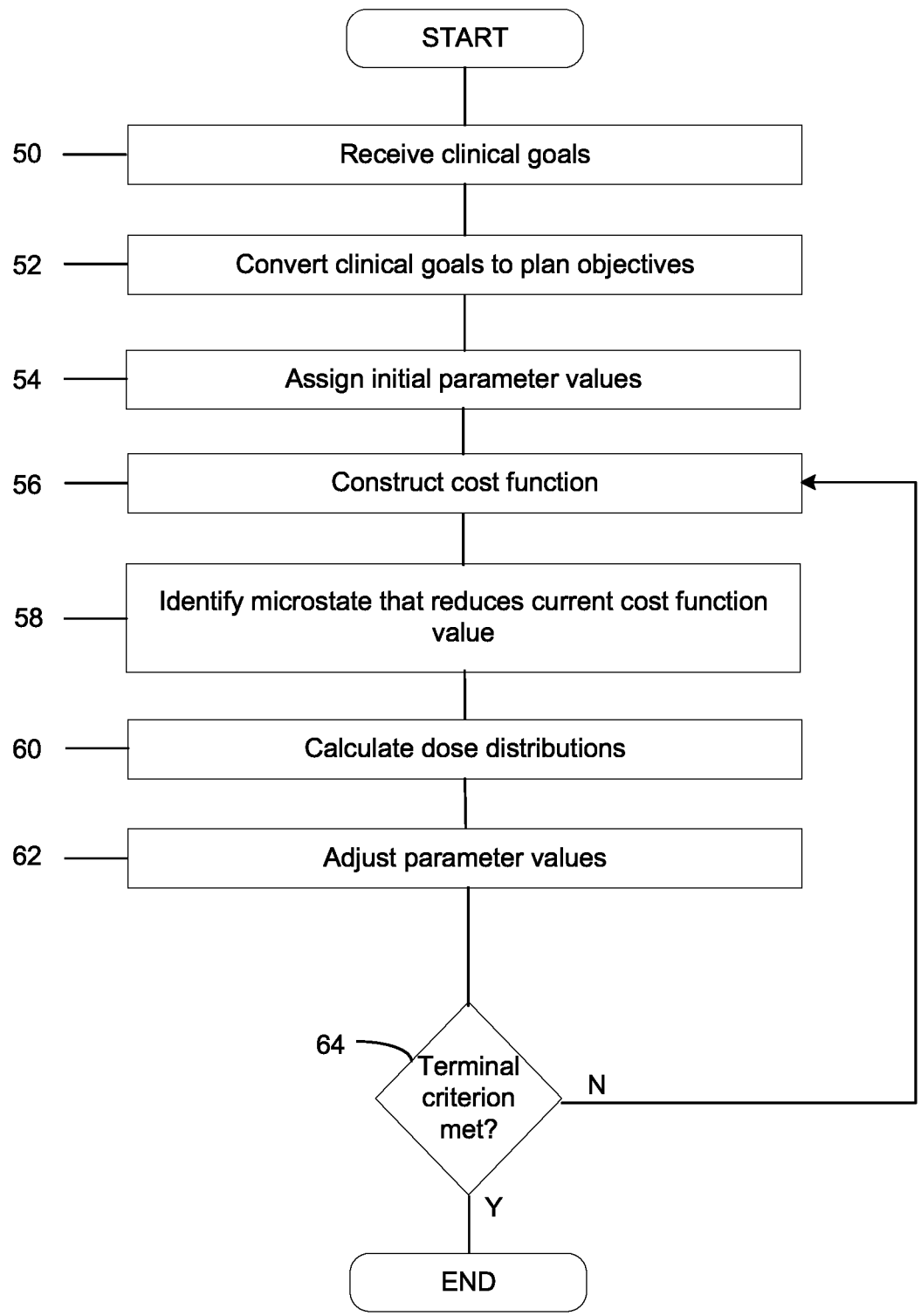
FIG. 3 is a flowchart depicting an exemplary method of optimizing an intensity-modulated radiation therapy (IMRT) treatment plan in accordance with an embodiment of the present invention.

Referring now to FIG. 3, an exemplary process flow is illustrated that may be performed, for example, by the IMRT treatment planning device 10 of FIG. 1 to implement an embodiment of the method described in this disclosure for developing an intensity-modulated radiation therapy (IMRT) treatment plan. The process begins at block 50, where a set of clinical goals are received regarding an IMRT treatment plan for a patient.

In block 52, as explained above, the clinical goals are converted to plan objectives, for example, dose-volume histogram (DVH)-based objectives. Each objective includes at least one free parameter, for example, a location or a weighting. An initial value is determined for each parameter in block 54.

A cost function is constructed, in block 56, with cost terms based on the plan objectives including the current set of objective parameters. In block 58, a search is performed, for example, using a gradient flow analysis of the cost function, to identify a microstate that results in a reduced or near-minimal value of the current cost function. A set of dose distributions is calculated, in block 60, as needed to evaluate how well the current microstate attains the specified clinical goals.

In block 62, the objective parameter values are individually adjusted, as explained above, so as to guide the dose distributions to better achieve the clinical goals. In block 64, a determination is made as to whether or not a terminal, or stopping, criterion has been met. If so, then the process ends. Otherwise, if the terminal criterion has not been met, then the process is repeated from block 56. As such, the metaoptimization process is iteratively carried out until the terminal criterion has been met.

Aspects of this disclosure are described herein with reference to flowchart illustrations or block diagrams, in which each block or any combination of blocks can be implemented by computer program instructions. The instructions may be provided to a processor of a general purpose computer, special purpose computer, or other programmable data processing apparatus to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that including one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, or the like, may be embodied in hardware, in software (including firmware, resident software, micro-code, etc.), or in any combination of software and hardware, including computer program products embodied in a computer-readable medium having computer-readable program code embodied thereon.

It will be understood that various modifications may be made. For example, useful results still could be achieved if steps of the disclosed techniques were performed in a different order, and/or if components in the disclosed systems were combined in a different manner and/or replaced or supplemented by other components. Accordingly, other implementations are within the scope of the following claims.

What is claimed is:

1. An apparatus for developing an intensity-modulated radiation therapy treatment plan, the apparatus comprising:
  a memory that stores machine instructions; and
  a processor that executes the machine instructions to:
    generate a cost function comprising a parameter value based on a plan objective;
    identify a microstate that results in a reduced value associated with the cost function, wherein the reduced value iteratively converges on a resultant value of the cost function;
    adjust a value associated with the parameter to improve a fulfillment level of a clinical goal associated with the plan objective; and
    generate an intensity-modulated radiation therapy treatment plan based on the resultant value.

2. The apparatus of claim 1, wherein the parameter value comprises a machine parameter value.

3. The apparatus of claim 2, wherein the machine parameter value comprises at least one of a selected field geometry and a selected monitor unit (MU) limit.

4. The apparatus of claim 1, wherein the parameter value comprises an optimal fluence and wherein the resultant value is a minimum value.

5. The apparatus of claim 4, wherein the processor further executes the machine instructions to convert said optimal fluence to a leaf sequence and to reduce a margin defined by the clinical goal.

6. The apparatus of claim 1, wherein the processor further executes the machine instructions to:
  estimate an initial value of the parameter value; and
  adjust the parameter value by projecting a gradient to estimate a goal value at which the clinical goal is achieved.

7. A method of developing an intensity-modulated radiation therapy treatment plan, the method comprising:
  determining a plurality of plan objectives based on a plurality of clinical goals;
  generating a cost function incorporating the plurality of plan objectives, wherein the cost function comprises cost terms each comprising a respective parameter value corresponding to the plan objectives;
  determining priority levels for the plurality of plan objectives;
  identifying a microstate that results in a reduced value associated with the cost function, wherein the reduced value iteratively converges on a resultant value of the cost function;
  adjusting parameter values of the cost terms based on to the microstate to improve a respective fulfillment level associated with the clinical goals according to the priority levels; and generating an intensity-modulated radiation therapy treatment plan based on the plurality of parameter values.

8. The method of claim 7, wherein the value of the cost function equals a sum of the cost terms.

9. The method of claim 8, wherein the cost terms minimize the value of the cost function when the corresponding plan objectives are attained, and wherein the resultant value of the cost function is a minimum value.

10. The method of claim 7, wherein the adjusting the parameter values of the cost terms comprises projecting a gradient associated with the cost terms to estimate a goal value at which the clinical goal is achieved.

11. The method of claim 7, wherein the adjusting the parameter values of the cost terms comprises estimating a resultant response of a dose distribution associated with a prospective adjustment of the respective parameter value based on an extrapolation corresponding to a localized response of the dose distribution.

12. The method of claim 7, further comprising assigning initial estimates to the plurality of parameter values based on an estimated dose distribution.

13. The method of claim 7, further comprising receiving the clinical goals as user input.

14. The method of claim 7, wherein the plurality of plan objectives are associated with a respective dose level corresponding to a point in a patient.

15. The method of claim 7, wherein the plurality of parameter values are associated with one selected from the group consisting of: a machine parameter; a selected field geometry; and a selected monitor unit (MU) limit.

16. A computer program product for developing an intensity-modulated radiation therapy treatment plan, the computer program product comprising:
a non-transitory, computer-readable storage medium encoded with instructions adapted to be executed by a processor to implement a method of:

determining a plurality of plan objectives based on a plurality of clinical goals;

generating a cost function incorporating the plurality of plan objectives, wherein the cost function comprises cost terms each comprising a respective parameter value corresponding to the plurality of plan objectives;

determining priority levels for the plurality of plan objectives;

identifying a microstate that results in a reduced value associated with the cost function, wherein the reduced value iteratively converges on a resultant value of the cost function;

adjusting the plurality of parameter values based on to the microstate to improve a respective fulfillment level associated with the plurality of clinical goals according to the priority levels; and generating an intensity-modulated radiation therapy treatment plan based on the plurality of parameter values.

17. The computer program product of claim 16, wherein the value of the cost function equals a sum of the cost terms.

18. The computer program product of claim 17, wherein the cost terms minimize the value of the cost function when the corresponding plan objectives are attained, and wherein the resultant value of the cost function is a minimum value.

19. The computer program product of claim 16, wherein the adjusting the plurality of parameter values comprises projecting a gradient associated with the cost terms to estimate a goal value at which the clinical goal is achieved.

20. The computer program product of claim 16, wherein the adjusting the plurality of parameter values comprises estimating a resultant response of a dose distribution associated with a prospective adjustment of the respective parameter value based on an extrapolation corresponding to a localized response of the dose distribution.

* * * * *